United States Patent [19]

Lipinski

[11] Patent Number: 4,556,670
[45] Date of Patent: Dec. 3, 1985

[54] SPIRO-3-HETERO-AZOLONES FOR TREATMENT OF DIABETIC COMPLICATIONS

[75] Inventor: Christopher A. Lipinski, Waterford, Conn.

[73] Assignee: Pfizer Inc., New York, N.Y.

[21] Appl. No.: 545,450

[22] Filed: Oct. 28, 1983

Related U.S. Application Data

[63] Continuation-in-part of Ser. No. 447,337, Dec. 6, 1982, abandoned.

[51] Int. Cl.[4] .................. C07D 277/34; C07D 233/38; C07D 263/44; A61K 31/415
[52] U.S. Cl. ..................................... 514/390; 514/369; 514/376; 548/147; 548/216; 548/313
[58] Field of Search ........................ 548/216, 147, 313; 424/270, 272, 273 R; 514/369, 376, 390

[56] References Cited

U.S. PATENT DOCUMENTS

| | | | |
|---|---|---|---|
| 2,872,454 | 2/1959 | Waring | 260/309.5 |
| 3,532,744 | 10/1970 | Fletcher, III et al. | 260/518 |
| 3,821,383 | 6/1974 | Sestanj et al. | 424/258 |
| 3,985,888 | 10/1976 | Carr et al. | 424/267 |
| 4,117,230 | 9/1978 | Sargas | 549/309 |
| 4,130,714 | 12/1978 | Sargas | 548/309 |
| 4,181,729 | 1/1980 | Sarges et al. | 424/273 R |
| 4,200,642 | 4/1980 | Schnur | 424/272 |
| 4,226,875 | 10/1980 | Schnur | 422/272 |
| 4,248,882 | 2/1981 | Sargas et al. | 424/273 R |
| 4,307,108 | 12/1981 | Belletire et al. | 424/274 |

FOREIGN PATENT DOCUMENTS

| | | | |
|---|---|---|---|
| 796069 | 6/1958 | United Kingdom | 548/147 |
| 2080304 | 2/1982 | United Kingdom | 548/147 |

OTHER PUBLICATIONS

J. A. Faust et al., "Anticonvulsants: Spirohydantoins and Derivatives of Tetrahydronaphthalene," *J. Amer. Pharm. Assoc.*, 44, 118–124, (1957).
H. R. Henze et al., "The Behavior of Certain 1,3-Indandiones in Attempted Hydantoin Formation," *J. Org. Chem.*, 17, 4–13, (1952).
R. C. Schnur et al., "Spiro Oxazolidinedione Aldose Reductase Inhibitors," *J. Med. Chem.*, 25, 1451–4, (1982).
R. Sarges et al., "Synthesis of Optically Active Spirohydantoins by Asymmetric Induction. Hydantoin Formation from Amino Nitriles and Chlorosulfonyl Isocyanate," *J. Org. Chem.*, 47, 4081–85, (1982).

*Primary Examiner*—Robert Gerstl
*Attorney, Agent, or Firm*—Charles J. Knuth; Peter C. Richardson

[57] ABSTRACT

Spiro-oxazolidones, -thiazolidones and -imidazolidones are disclosed which are useful as aldose reductase inhibitors and as therapeutic agents for the treatment of complications arising from diabetes. Pharmaceutical compositions containing the spiro compounds and a method of treating diabetic complications are also disclosed.

60 Claims, No Drawings

SPIRO-3-HETERO-AZOLONES FOR TREATMENT OF DIABETIC COMPLICATIONS

This application is a continuation-in-part of Ser. No. 447,337, filed Dec. 6, 1982 and now abandoned.

BACKGROUND OF THE INVENTION

This invention relates to novel spiro-3-heteroazolidindiones useful in the treatment of certain chronic complications arising from diabetes mellitus, such as diabetic cataracts, retinopathy and neuropathy, to pharmaceutical compositions containing such compounds and to a method of using these compounds.

In the past various attempts have been made to obtain more effective oral anti-diabetic agents. Generally these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. U.S. Pat. No. 4,117,230 teaches the use of certain hydantoins for treating complications of diabetes as aldose reductase inhibitors. Such aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way unwanted accumulations of galactitol in the lens of galactosemic subjects and of sorbitol in the lens, peripheral nervous cord and kidneys of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

SUMMARY OF THE INVENTION

The compounds of the present invention are spirohetero-azolidindiones of the formula

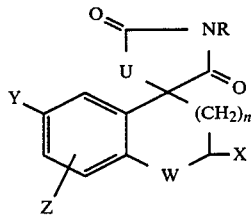

I and the pharmaceutically acceptable salts thereof, wherein U is oxygen, sulfur or nitrogen substituted with hydrogen or alkyl having 1-4 carbon atoms; n is zero or one; R is hydrogen or alkyl having 1-4 carbon atoms; W is carbonyl or hydroxymethylene; X is hydrogen, bromo, chloro, iodo, alkyl having 1-4 carbon atoms, dimethyl or $(CH_2)_mQ$ wherein m is 1 or 2 and Q is phenyl or halophenyl, with the proviso that when X is dimethyl, n is one; Y is hydrogen, halo, nitro, trifluoromethyl, alkoxy having 1-4 carbon atoms or alkyl having 1-4 carbon atoms; Z is hydrogen, halo, nitro, trifluoromethyl, alkoxy having 1-4 carbon atoms or alkyl having 1-4 carbon atoms, with the proviso that if either Y or Z is nitro the other is hydrogen.

Embraced by the present invention are compounds wherein U is oxygen, particularly when n is one, more particularly when W is carbonyl. Preferred compounds are those wherein R is hydrogen, preferably wherein X is methyl, Y is fluoro and Z is hydrogen.

Also embraced by the present invention are compounds wherein U is nitrogen substituted by hydrogen, n is one, W is carbonyl and R is alkyl, particularly when R is methyl. Preferred are compounds wherein X is methyl, preferably when Z is hydrogen, more preferably when Y is fluoro.

A group of compounds included in the present invention are those wherein U is nitrogen substituted with a hydrogen and n is zero. Within the group, W may be carbonyl and preferably X and Z are hydrogen and Y is hydrogen or fluoro. W may also be hydroxymethylene and preferably X and Z are each hydrogen and Y is hydrogen or fluoro.

Another included group of compounds within the present invention are those wherein U is nitrogen substituted with a hydrogen or alkyl, preferably methyl, and n is one. W may be carbonyl and preferably X is hydrogen. Preferred compounds are those wherein Y and Z are hydrogen, wherein Y is fluoro and Z is hydrogen, and the positively rotating enantiomer thereof wherein R is hydrogen. Also, preferably X is bromo. Preferred compounds are those wherein Y and Z are each hydrogen. Additionally, preferably X is methyl. Preferred compounds are those wherein Y and Z are each hydrogen and the positively rotating enantiomer thereof. Furthermore, X may be dimethyl; preferably Y is chloro and Z is hydrogen. Also, W may be hydroxymethylene and preferably X is hydrogen and further preferred Y is hydrogen or fluoro and Z is hydrogen. Additionally, preferably X is methyl, Y is fluoro and Z is hydrogen and the positively rotating enantioner thereof.

Both mixtures of optically active isomers and partially or completely optically resolved isomers of the compounds claimed herein are within the scope of the present invention.

Also embraced by the present invention are pharmaceutical compositions comprising a pharmaceutically acceptable carrier or diluent and a compound of formula I. Preferred compositions are those wherein U is nitrogen substituted with a hydrogen, n is one, R is hydrogen, W is carbonyl, X and Z are hydrogen, Y is fluoro and the compound is the positively rotating enantiomer. Also preferred compositions are those wherein U is nitrogen substituted with a hydrogen, n is one, R is hydrogen, W is carbonyl, X is methyl and Y is fluoro, and more preferred, the compound is the positively rotating enantiomer.

The present invention further comprises a method of treating a diabetic host for diabetes-associated complications which comprises administering to the host an effective amount of a compound of formula I. A preferred method is one wherein n is one, W is carbonyl, R is hydrogen, X and Z are hydrogen, Y is fluoro and the compound is the positively rotating enantiomer. Also preferred is the method wherein n is one, W is carbonyl, R is hydrogen, X is methyl, Z is hydrogen, and Y is fluoro and more preferred, the compound is the positively rotating enantiomer.

Also included in the present invention are a compound of the formula

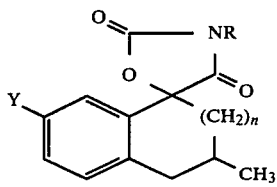

wherein
n is zero or one
R is hydrogen or alkyl having 1-4 carbon atoms; and
Y is hydrogen, halo, nitro, trifluoromethyl, alkoxy having 1-4 carbon atoms or alkyl having 1-4 carbon atoms.

Preferred are compounds wherein n is one, particularly wherein R is hydrogen, and more particularly wherein Y is fluoro.

DETAILED DESCRIPTION

The numbering system of the spiro compounds of formula I where n is zero (IA) is as shown. These

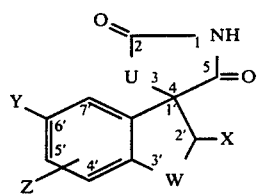

compounds (IA) are 6'-Y-4' or 5'-Z-2'-X-spiro[imidazolidine-, oxazolidine- or thiazolidine-4,1'-indan]2,5-dione derivatives.

The numbering system of compounds of formula I wherein n is one (IB) is as shown. These compounds

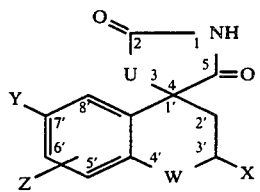

are, when W is hydroxymethylene, 4'-hydroxy-7'-Y-6' or 5'-Z-3'-X-spiro[imidazolidine-, oxazolidine- or thiazolidine-4,1'-1',2',3'-4'-tetrahydronaphthalene]2,5-diones. When W is carbonyl, these compounds are 7'-Y-6' or 5'-Z-3'-X-spiro[imidazolidine-, oxazolidine-or thiazolidine-4,1'-3'H-1',2'-dihydronaphthalen-4'-one]2,5-diones.

Compounds of formula I can be prepared by two different synthetic schemes (A and B)(U is NH). Starting materials for Scheme A are 1-indanones and 1-tetralones (VI). 1-Indanones are well known compounds and those starting 1-indanones not described in the literature may be made by routes analogous to those used to prepare the known compounds.

A particularly useful route used to prepare 1-indanones is by the cyclization of a hydrocinnamic acid derivative. These intermediates in turn are prepared by hydrogenation of the cinnamic acid which in turn is prepared by condensation of an appropriate benzaldehyde derivative with malonic acid followed by decarboxylation.

A representative procedure is that of R. Fuchs and J. A. Caputo, J. Org. Chem., 31, 1524–6(1966).

Starting benzaldehydes with the appropriate substitution pattern are known compounds. Using the appropriate benzaldehyde, the desired 1-indanones (VI) can be prepared.

1-Tetralones are also well known compounds and those starting 1-tetralones not described in the literature may be made by routes analogous to those used to prepare the known compounds.

A particularly useful route to prepare 1-tetralones is the method of L. F. Fieser and A. M. Seligman, J. Amer. Chem. Soc., 60, 170–6 (1938) which utilizes the cyclization of an appropriate 4-phenyl butyric acid. These acids in turn may be prepared by Clemmenson reduction of 3-benzoylpropionic acids. 3-Benzoyl propionic acids having the appropriate substitution pattern are known, can be prepared by literature methods or according to the procedure to be discussed below. These acids are the precursors to the 1-tetralones employed in Scheme A. Alternatively, by use of Scheme B these same acid intermediates allow preparation of final products of formula I with different substitution patterns.

A particularly useful route to 3-benzoylpropionic acids comprises condensation of a benzaldehyde derivative with acrylonitrile or alpha-substituted acrylonitrile in the presence of potassium cyanide in dimethyl formamide to generate a 3-benzoylpropionitrile which is then hydrolyzed in concentrated mineral acids such as hydrochloric acid to the corresponding 3-benzoylpropionic acid.

A representative procedure for the condensation step is that of H. Stelter and M. Schrecke, Chem. Ber., 107 210–14 (1974).

It will be recognized that 3-benzoylpropionic acids substituted in the 2-position with other than hydrogen lead to 3-benzoylpropionic acids that are useful in the synthesis of tetrahydronaphthalene final products by Scheme A.

3-Substituted-3-benzoylpropionic acids are also useful in preparation of tetrahydronaphthalene final products of formula I via scheme A. 3-Substituted-3-benzoylpropionic acids not described in the literature may be made by procedures closely analogous to those used to prepare known compounds by the method of F. J. McEvoy and G. R. Allen Jr., J. Org. Chem., 38, 4044–48 (1973).

It will be recognized that 3-benzoylpropionic acids substituted in the 2-position with other than hydrogen lead to 3-benzoylpropionic acids which are useful in the synthesis of tetrahydronaphthalene final products by Scheme B. This route is particularly useful because of the ready availability of substituted benzaldehydes and because alpha-substituted acrylonitriles (X other than hydrogen) such as methacrylonitrile are commercially available or can be made by the general procedure of R. B. Miller and B. F. Smith, Syn. Comm., 413–17 (1973). 2-Substituted-3-benzoylpropionic acids also can be made by use of this route.

3-Benzoylpropionic acids may also be prepared from known substituted bromobenzenes. The bromobenzene derivative is converted to a Grignard reagent and then to a cadminum reagent which is reacted with the half acid halide, half ester of succinic acid to afford the ester of the 3-benzoylpropionic acid. The ester may than be cleaved to the free acid by basic hydrolysis.

This procedure is particularly useful for preparation of tetrahydronaphthalene final products where X is dimethyl. For example alpha, alpha- dimethyl-succinate may be converted into beta-carbomethoxyisovaleryl chloride (X is dimethyl) according to the procedure of C. C. Price and T. Padmanathan, J. Org. Chem., 30, 2064–67 (1965).

This acid chloride may be reacted with various bromobenzene derivatives to provide 3,3-dimethyl-3-substituted benzoyl propionic acids. These derivatives may be used in Scheme A to provide tetrahydronaphthalene final products where X is dimethyl.

A useful procedure for preparation of 3-benzoylpropionic acids is the Friedel-Craft acylation of a benzene derivative to give directly a 3-benzoylpropionic acid according to the general procedure of L. F. Fieser and E. B. Heishberg, J. Amer. Chem. Soc., 58, 2314 (1936). The nature of the product will be determined both by the directive effect of the Y and Z substituents in the benzene ring and also by the nature of X if it is other than hydrogen. Where X is dimethyl, the benzoylpropionic acid formed is that in which the gem dimethyl moiety is adjacent to the carboxyl group rather than ketone carbonyl. Therefore using as-dimethylsuccinic anhydride, 3-benzoyl-2,2-dimethylpropionic acids may be prepared which, using Scheme B, can be converted to tetrahydronaphthalene final products where X is dimethyl.

A useful method for increasing the versatility of the synthesis of 3-benzoylpropionic acids involves converting the ketone carbonyl of the initially formed 3-benzoylpropionic acid into a powerfully election withdrawing group by complexation with $AlCl_3$ such that the aromatic ring can be halogenated at a position meta to the $AlCl_3$ complexed carbonyl group.

The method is particular useful for conversion of 3,3-dimethyl-3-(4-substituted-benzoyl)propionic acids into 3,4-disubstituted benzoyl derivatives. These may in turn be converted using Scheme B into 6', 7'-disubstituted tetrahydronaphthalenes.

An additional useful method for the preparation of 3-benzoylpropionic acids consists of the reaction of an aryl Grignard reagent prepared from an aryl iodide such as commercially-available iodobenzene derivatives with a silylated gamma-butyrolactone followed by oxidation.

2-Benzoylacetic acids and their ester derivatives can be useful as starting materials to provide dihydroindene final products.

The compounds of formula VI may be converted to the corresponding compounds of formula II wherein U is nitrogen substituted with a hydrogen (NH) or lower alkyl group (N—R) such as N—$CH_3$, oxygen (O) or sulfur (S). In synthetic scheme A, the preparation of compounds of formula II is known (see U.S. Pat. No. 4,117,230 (U=NH). The preparation of compounds of formula II wherein U=NR is carried out from compounds of formula VI via the reaction with chlorosulfonyl isocyanate of the carboximine addicts of compounds of formula VI with amines ($H_2NR$) according to the procedure described by Reinhard Sarges, Harry R. Howard Jr., and Paul R. Kelbaugh, J. Org. Chem., 1982, 47, 4081-5.

Compounds of formula I wherein U is oxygen can be prepared by either Synthetic Scheme A or B in a manner similar to that when U is NH. Of course, the reagents employed with the carbonyl presursor (VI or IV) to form the oxazolidinedione ring (U is oxygen) are different than the reagents which react to form the hydantoin ring (U is NH). The compounds of formula II wherein U is oxygen are known or can be prepared from the corresponding 1-tetralone or 1-indanone (VI) by the methods described in U.S. Pat. No. 4,226,875. The synthesis of certain spiro oxazolidinones is disclosed in R. C. Schnur et al., Journal of Medicinal Chemistry, 25, 1451–4 (1982).

These compounds of formula II are reacted at about 0° to 60° C., preferably about 25° C., with a perfluorocarboxylimine having N-dialkylsilyl and an O-dialkylsilyl groups, for example N-dimethylsilyl-O-dimethylsilylperfluoro-acetic acid imine, which acts as a protecting group for the imide nitrogen, in a nonreactive halogenated solvent hydrocarbon such as chloroform which does not interfere with the subsequent halogenation reaction.

The in situ halogenation is preferably carried out with a molecular halogen such as bromine, chlorine or iodine, more preferably bromine. For example, in situ bromination with bromine at a temperature range of about 25° to 100° C., preferably about 60° C. results in the 4'-bromo derivative III.

The 4'-halo derivative III is hydrolyzed in water having a pH range of about 1 to 7, preferably about 4 at a temperature range of about 0° to 60° C., preferably about 25° C. The resulting alcohol I (W is hydroxymethylene) may be further oxidized to the corresponding ketone (I, W is carbonyl) using any convenient oxidizing agent such as chromium trioxide in acetic acid at about 0° to 60° C., preferably about 25° C.

Compounds of formula I wherein W is carbonyl and X is hydrogen can be halogenated to form an alpha-halo ketone wherein X is halo. The halogenation can be performed with a molecular halogen ($Br_2$, $Cl_2$, $I_2$) in a suitable solvent such as a lower alkane hydrocarbon acid of 1–6 carbon atoms, preferably of 1–4 carbon atoms, more preferably acetic acid, using a mineral acid catalyst such as hydrobromic acid at between about 0° to 100° C., preferably 25°–80° C.

Alternatively, the compound of formula I wherein X is hydrogen and W is carbonyl can be halogenated so that X is halo by first treating I with a perfluorocarboxylimine having N-trialkylsilyl and O-trialkylsilyl groups, for example, N-trimethylsilyl-O-trimethylsilyperfluoroacetic acid imine in a nonreactive halogenated solvent such as chloroform followed by reaction with the desired molecular halogen, as previously described for the conversion of II to III in Scheme A.

Alternatively, for compounds of formula I, wherein U is NH, Synthetic Scheme B may be employed. The corresponding benzene-gamma-oxo acids IV, which are known or can be prepared by procedures analogous to those described for the known compound, are reacted with an ammonium salt such as ammonium carbonate and an alkali metal cyanide such as sodium or potassium cyanide, preferably sodium cyanide, in an aqueous solution such as water or a water-alcohol mixture, e.g., water-ethanol, at a pH of about 9 to 10, preferably 10 and a temperature range of about 50° to 100° C., preferably about 70° C. to obtain the compound of formula V (U is NH).

The resulting condensation product V is reacted with a strong Lewis acid such as polyphosphoric acid at a temperature range of 100° to 200° C., preferably about 150° C. to obtain I. Alternatively, concentrated sulfuric acid (6 to 9M, preferably 9M) at about 60° to 180° C., preferably about 120° C. can be employed. Other strong Lewis acids such as mineral acids, aluminum trichloride, ferric chloride and the like can also be employed.

The compound of formula I wherein W is carbonyl can be reduced by any of a variety of commonly used reducing agents such as lithium aluminum hydride, sodium borohydride, aluminum isopropoxide and the like. Preferred solvents for lithium aluminum hydride related derivatives are non-hydroxylic solvents such as ether, dioxane or tetrahydrofuran and preferred temperatures are about −30° C. to 25° C., preferably about 0° C. Preferred solvents for sodium borohydride and related derivatives are lower alkanol solvents such as methanol or ethanol at about 0° to 60° C., preferably about 25° C. Preferred solvents for reduction with aluminum isopropoxide is isopropyl alcohol at reflux with slow distillation of the acetone byproduct.

In addition, compounds of formula I prepared according to Scheme B wherein W is carbonyl and X is hydrogen can of course be converted to the alpha-halo ketone according to the same procedure previously described.

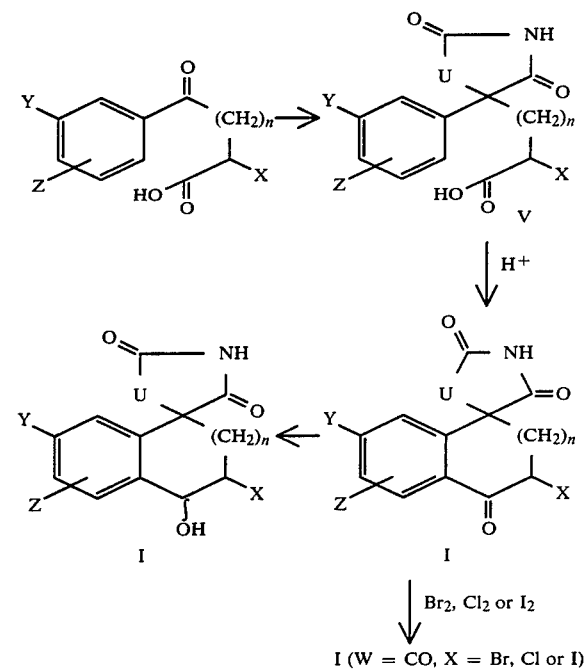

Alternatively, compounds of formula I wherein U is oxygen can also be prepared using Synthetic Scheme B. The corresponding benzene-gamma-oxo acids IV which are known or can be prepared by procedures

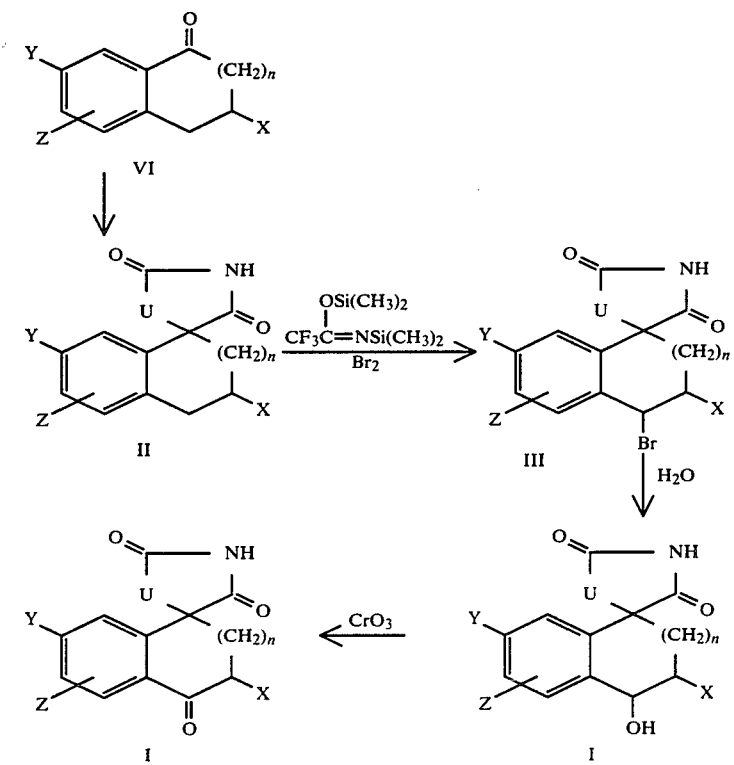

closely analogous to those described for known compounds are reacted with a trialkylsilyl cyanide (R')$_3$SiCN, wherein R' is lower alkyl, to form a cyano trialkylsilyloxy derivative according to the general procedure described in U.S. Pat. No. 4,267,342.

Compounds of formula I wherein U is S can be prepared by Synthetic Schemes A or B in a manner similar to that used to prepare the compounds of formula I wherein U is NH. Advantage is taken of the preparation of cyanotrialkylsilyloxy derivatives which are intermediates in the preparation of compounds of formula I wherein U is O. These cyanotrialkylsilyloxy derivatives may be converted by similar methods to thiazolidinedione intermediates of structure II wherein U is S (Synthetic Scheme A) and intermediates of structure V wherein U is S (Synthetic Scheme B).

Intermediates of structure II wherein U is S (Synthetic Scheme A) and intermediates of structure V wherein U is S (Synthetic Scheme B) may be converted to final products of structure I as previously described for U being NH.

Because of the acidic hydrogen atom in the spiroheterocyclic ring of the compounds of formula I, salts ma be formed with pharmaceutically acceptable cations by conventional methods. Thus, these salts may be readily prepared by treating the compound of formula I with an aqueous solution of a base having the desired pharmaceutically acceptable cation and evaporating the resulting solution to dryness, preferably under reduced pressure. Alternatively, a lower alkyl alcohol solution of the compound of formula I may be mixed with an alkoxide of the desired metal and the resulting solution subsequently evaporated to dryness. Suitable pharmaceutically acceptable cations for this purpose include, but are not limited to, alkali metal cations such as potassium and sodium, alkaline earth metal cations such as calcium and magnesium ammonium, lower alkanolammonium and other cations derived from pharmaceutically acceptable organic amines which form water-soluble amine addition salts.

It is to be understood that by use of the term pharmaceutically acceptable salts in the disclosure and claims hereof it is meant to embrace both the acid addition salts and the salts formed with appropriate cations, as described above.

Also included within the scope of this invention are derivatives which are metabolized in-vivo to compounds of formula IA or IB. In particular are disclosed derivatives in which the acidic NH group at position 1 in formula IA and IB is converted to an N-R group wherein R is a lower alkyl moiety generally of 1-4 carbon atoms, preferrably methyl. Such compounds can be made by alkylating a compound of formula IA or IB in the presence of a suitable base with an alkylating agent. Suitable bases include but are not limited to alkali metal hydroxides such as sodium or potassium hydroxide, alkali metal carbonate or alkoxide such as sodium carbonate or sodium ethoxide or alkali metal hydride in a non-protic solvent such as sodium hydride in N,N-dimethylformamide at a temperature of between about 0° and 50° C., preferably about 25° C. Suitable alkylating agents include but are not limited to methyl iodide, dimethylsulfate, ethylbromide. Alkylating agents that can be used in the absence of base include diazoalkanes such as diazomethane.

A particularily convenient method of preparing derivatives in which the acidic NH group at position 1 in formula IA and IB is converted to an N-R group consists of dissolving the compound of formula Ia or Ib in dry N,N-dimethylformamide and adding 1 equivalent of sodium hydride at a temperature of between about 0° and 50° C., preferably about 25° C. The reaction is stirred until foaming stops. One molar equivalent of the alkylating agent such as a lower alkyl halide or alkyl sulfate is added dropwise and the reaction is stirred until alkylation is complete. A preferred alkylating agent is methyl iodide and reaction time with this halide at about 25° C. is about one hour. The reaction may be worked up by pouring onto ice-water. The alkylated products may be separated from any starting materials by taking advantage of the acidity of the starting compounds of formula Ia or Ib as opposed to the neutral character of the alkylated products. For example the compound of Example 28 has $pK_A$ of about 8.3 in water and any unreacted compound can be removed by partitioning crude product between an organic solvent such as ethyl acetate or methylene chloride and an aqueous base solution. The alkylated product is soluble in the organic solvent while any unreacted starting material is soluble in the aqueous base.

The novel compounds of formula I and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention and alleviation of such conditions. The compound may be administered to a subject in need of treatment by a variety of conventional routes of administration, including orally, parenterally and topically. In general, these compounds will be administered orally or parenterally at dosages between about 0.05 and 25 mg./kg. body weight of the subject to be treated per day, preferably from about 0.1 to 10 mg./kg. However, some variation in dosage will necessarily occur depending on the condition of the subject being treated. The person responsible for administration will, in any event, determine the appropriate dose for the individual subject.

The novel compound of the invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral adminstration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Compounds of formula I may not only be advantageously employed for the preparation of aqueous pharmaceutical compositions for parenteral administration, as described above, but more particularly for the preparation of pharmaceutical compositions suitable for use as ophthalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts the compounds of this invention are administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.). The ophthalmic preparation will contain a compound of formula I or a pharmaceutically acceptable salt thereof in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potasssium borate, sodium and potassium carbonate, sodium acetate, sodium biphosphate and the like, in amounts sufficient to maintain the pH at between about 6 and 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve and lens of acutely streptozotocinized, i.e. diabetic, rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; (5) measuring their ability to delay cataract formation and reduce the severity of lens opacities in chronic galactosemic rats; (6) measuring their ability to prevent sorbitol accumulation and cataract formation in isolated rat lens incubated with glucose; and (7) measuring their ability to reduce already elevated sorbitol levels in isolated rat lens incubated with glucose.

The present invention is illustrated by the following examples. It will be understood, however, that the invention is not limited to the specific details of these examples. Proton nuclear magnetic resonance spectra (NMR) were measured at 60 MHz (unless otherwise indicated) for solutions in perdeuterodimethyl sulfoxide (DMSO-$d_6$) and peak positions are expressed in parts per million (ppm) downfield from tetramethylsilane. The peak shapes are denoted as follows: s, singlet; d, doublet; t, triplet; q, quartet; m, multiplet; b, broad.

EXAMPLE 1

3'-Hydroxy-spiro[imidazolidine-4,1'-indan]2,5-dione

Spiro[imidazolidine-4,1'-indan]2,5-dione, (C.A. reg. no. 6252-98-8) (6.06 g, 30 mmol) was combined with 7.95 ml (30 mmol) bis(trimethylsilyl)trifluoroacetamide and 4.8 g (30 mmol) bromine in 50 ml chloroform and heated to reflux. Decolorization occurred during the 18 hour reaction. The reaction mixture was cooled to 25° C. and after 45 minutes stirring a solid which had crystallized was collected by filtration to give 2.45 g (29%) of crude 3'-bromo-spiro[imidazolidine-4,1'-indan]2,5-dione. The chloroform mother liquors deposited an additional 2.18 g (26% yield), mp 58°-65° C. Two grams (7.1 mmol) of material, mp 58°-65° C., was combined with 25 ml water to give a slurry. Following stirring for 22 hours the resultant solid was collected by filtration and dried to give 0.52 g (33% yield) of the title compound: mp 260°-263° C.

Anal. Calcd for $C_{11}H_{10}N_2O_3$: C, 60.55; H, 4.62; N, 12.84. Found: C, 60.84; H, 4.74; N, 12.80.

EXAMPLE 2

Spiro[imidazolidine-4,1'-indan-3'-one]2,5-dione

3'-Hydroxy-spiro[imidazolidine-4,1'-indan]2,5-dione (1.2 g, 5.5 mmol) was combined with 0.550 g (5.5 mmol) of chromium trioxide in 20 ml glacial acetic acid at 25° C. As dissolution occurred the reaction mixture darkened and the temperature rose to 39° C. After 10 minutes the reaction mixture was concentrated in vacuo to a gummy solid. Following trituration with water, a white solid was isolated by filtration. The solid was dissolved in tetrahydrofuran, filtered and the filtrate concentrated in vacuo to give 0.470 g (39% yield) of the title compound: mp 253°–256° C.

NMR (DMSO-d$_6$): 11.13 (bs, 1H), 8.50 (bs, 1H), 7.97–7.43 (m, 4H) and δ3.0 (d, 2H) ppm.

Anal. Calcd for $C_{11}H_8N_2O_3$: C, 61.11; H, 3.73; N, 12.96. Found: C, 60.54; H, 4.02; N, 13.09.

EXAMPLE 3

Spiro[imidazolidine-4,1'-indan-3'-one]2,5-dione 2,5-Dioxo-4-phenyl-4-imidazolidineacetic acid (C.A. reg. no. 62985-01-7) was suspended in 15 ml polyphosphoric acid at 150° C. Dissolution gradually occurred and after 2 hours at 150° C. the reaction mixture was cooled to 25° C. and diluted with 15 ml water. A solid formed slowly and was collected by filtration, washed with water, dried and recrystallized from water to give 0.210 g (40% yield) of the title compound: mp 268°–270° C.

Anal. Calcd for $C_{11}H_8N_2O_3$: C, 61.11; H, 3.73; N, 12.96. Found: C, 60.89; H, 3.87; N, 12.98.

EXAMPLE 4

3'-Hydroxy-6'-fluoro-spiro[imidazolidine-4,1'-indan]2,5-dione

6'-Fluoro-spiro[imidazolidine-4,1'-indan]-2,5-dione, (C.A. reg. no. 66892-38-4)(1.1 g, 5 mmol) was combined with 2.65 ml (10 mmol) bis-(trimethylsilyl) trifluoroacetamide, 0.8 g (5 mmol) bromine and 30 ml ethylene dichloride and heated at reflux for 2.5 hours. During this time color was lost from the reaction mixture. The reaction mixture was concentrated in vacuo to an amber oil which was diluted with 10 ml water. Over a period of 16 hours at 25° C. a solid gradually formed. This material was isolated by filtration and dried in vacuo at 100° C. to give 1.0 g (85% yield) of the title compound: mp 209°–211° C.

EXAMPLE 5

6'-Fluoro-spiroimidazolidine-4,1'-indan-3'-one]2,5'-dione

3'-Hydroxy-6'-fluoro-spiro[imidazolidine-4,1'indan]-2,5-dione (1.0 g, 4.2 mmol) was combined with 0.424 g (4.2 mmol) chromium trioxide in 25 ml glacial acetic acid and was heated at 100° C. for 1 hour. The reaction was concentrated in vacuo to a dark foam and 25 ml of water was added. A solid formed and was collected by filtration, washed with water, decolorized in 1:1 by volume methanol-water with activated charcoal and recrystallized from 1:1 methanol-water to give 0.305 g (31% yield) of the title compound: mp 310° C., with decomposition.

Anal. Calcd for $C_{11}H_7FN_2O_3$: C, 56.42; H, 3.01; N, 11.96. Found: C, 55.85; H, 3.22; N, 12.06.

EXAMPLE 6

4'-Hydroxy-spiro[imidazolidine-4,1'-1',2',3',4'-tetrahydronaphthalene]2,5-dione

Spiro[imidazolidine-4,1'-1',2',3',4'-tetrahydronaphthalene]2,5-dione (C.A. reg. no. 57998-96-6) (4.33 g, 20 mmol) was combined with 10.40 ml (40.4 mmol) bis(-trimethylsilyl) trifluoroacetimide and 3.69 g (23.1 mmol) bromine in 40 ml chloroform solvent at 25° C. The slurry was stirred for 60 hours with observed decolorization. The reaction was filtered and the filtrate was concentrated in vacuo to an oil. To the oil was added 15 ml of water and the resultant gummy solid was triturated for 22 hours. A solid was collected by filtration and dried to give 3.3 g (82% yield) of the title compound: mp 180°–185° C.

Anal. Calcd for $C_{12}H_{12}N_2O_3$: C, 62.06; H, 5.21; N, 12.06. Found: C, 62.08; H, 4.78; N, 12.46.

EXAMPLE 7

Spiro[imidazolidine-4,1'-3'H-1',2'-dihydronaphthalen-4'-one ]-2,5-dione

4'-Hydroxy-spiro[imidazolidine-4,1'-1',2',3',4'-tetrahydronaphthalene]2,5-dione (10.0 g, 43.1 mmol) was combined with 4.34 g (43.4 mmol) of chromium trioxide in 80 ml glacial acetic acid and stirred at 25° C. for 1 hour. The reaction mixture was concentrated in vacuo and the resultant solid was triturated with water, collected by filtration and washed with water. The precipitate was dissolved in isopropanol and decolorized with activated charcoal. The solvent was removed in vacuo and the solid crystallized from isopropanol to give 4.0 g (40% yield) of the title compound: mp 256°–258° C.

Anal. Calcd for $C_{12}H_{10}N_2O_3$: C, 62.60; H, 4.38; N, 12.17. Found: C, 62.84; H, 4.75; N, 12.15.

EXAMPLE 8

Spiro[imidazolidine-4,1'-3'H-1',2'-dihydronaphthalen-4'-one]2,5-dione 2,5-Dioxo-4-phenyl-4-imidazolidinepropionic acid (C.A. reg. no. 30741-72-1)(2.48 g, 10 mmol) was warmed in 25 ml concentrated sulfuric acid first at 90° C. for 1 hour and then at 120° C. for 45 minutes and poured onto 200 g ice. The resultant solid was collected by filtration and dried in vacuo at 100° C. for 60 hours to give 1.85 g of crude product, mp 144°–149° C. The material was decolorized from a solution in isopropanol with activated charcoal and recrystallized from isopropanol to give 1.11 (48% yield) of the title compound: mp 261°–263° C.

Anal. Calcd for $C_{12}H_{10}N_2O_3$: C, 62.60; H, 4.38; N, 12.17. Found: C, 62.34; H, 4.51; N, 12.16.

EXAMPLE 9

Spiro[imidazolidine-4,1'-3'H-1',2'-dihydronaphthalen-4'-one]2,5-dione 2,5-Dioxo-4-phenyl-4-imidazolidinepropionic acid (C.A. reg. no. 30741-72-1)(2.48 g, 10 mmol) was suspended in 25 ml polyphosphoric acid at 150° C. Dissolution gradually occured and after 135 minutes the reaction was cooled to 25° C. Water (75 ml) was added and the resultant crude solid was isolated by filtration. This solid material was decolorized with activated charcoal as a solution in isopropanol and recrystallized from isopropanol to give 450 mg (17% yield) of the title compound: mp 262°–263° C.

NMR (DMSO-d$_6$): δ10.98 (bs, 1H), 8.65 (bs, 1H), 8.03–7.30 (m, 4H) and 3.07–2.23 (m, 4H)ppm.

EXAMPLE 10

7'-Fluoro-spiro[imidazolidine-4,1'-3'H-1',2'-dihydronaphthalen-4'-one]2,5-dione 2,5-Dioxo-4-m-fluorophenyl-4-imidazolinepropionic acid (1.33 g, 5 mmol) was combined with 15 ml polyphosphoric acid and heated at 150° C. for 1.5 hours. The reaction mixture was cooled to 0° and was diluted with water. A dark solid was collected by filtration and was partitioned between ethyl acetate and dilute aqueous sodium hydroxide (pH 8). The ethyl acetate layer was extracted with aqueous 10% sodium hydroxide and the combined aqueous layers were decolorized with activated charcoal and brought to pH 3 with concentrated hydrochloric acid. The water was evaporated in vacuo and the resultant white solid was triturated with boiling isopropanol to remove sodium chloride. The isopropanol solution was filtered and concentrated in vacuo to give 115 mg of the title compound as a white foam. NMR (DMSO-d$_6$): δ8.55 (bs, 1H), 8.02 (q, 1H), 7.37 (m, 1H), 7.17 (q, 1H), 3.15–2.96 (m, 1H), 2.75–2.6 (m, 1H) and 2.45–2.3 (m, 2H)ppm.

EXAMPLE 11

7'-Fluoro-spiro[imidazolidine-4,1'-3'H-1',2'-dihydronaphthalen-4'-one]2,5-dione 2,5-Dioxo-4-m-fluorophenyl-4-imidazolidinepropionic acid (68.55 g, 0.26 mol) was combined with 500 ml concentrated sulfuric acid and heated at 75°–77° C. for 2.5 hours. The reaction mixture was cooled to 25° C. and poured onto ice to precipitate a solid which was isolated by filtration. The solid was dissolved in 800 ml methanol and decolorized with DARCO G-60 activated charcoal. The methanol was removed in vacuo to leave a solid which was triturated with 75 ml methanol, then collected by filtration. Following washing with 30 ml water, the solid was dried in vacuo at 80° C. for 20 hours to give 52.07 g (81% yield) of the title compound: mp 229°–231° C.

Anal. Calcd for $C_{12}H_9FN_2O_3$: C, 58.07; H, 3.65; N, 11.29. Found: C, 57.86; H, 3.59; N, 11.39.

EXAMPLE 12

3'-Bromo-spiro[imidazolidine-4,1'-3'H-1',2'-dihydronaphthalen-4'-one]-2,5-dione

Spiro[imidazolidine-4,1'-3'H-1',2'-dihydronaphthalen-4'-one]-2,5-dione (2.08 g, 9 mmol) was combined with 2.4 ml (9 mmol) bis(trimethylsilyl) trifluoroacetamide and 20 ml chloroform and was heated at reflux for 1 hour. Bromine (1.5 g, 9.4 mmol) in 10 ml chloroform was added and reflux was continued for 40 minutes at which point a white precipitate began to form. After an additional 10 minutes at reflux the reaction was cooled to 25° C. and the resultant solid was isolated by filtration and dried to give 1.27 g (46% yield) of the title compound: mp 221°–224° C.

Anal. Calcd for $C_{12}H_9BrN_2O_3$: C, 46.63; H, 2.93; N, 9 06. Found: C, 46.42; H, 3.10; N, 9.12.

EXAMPLE 13

7'-Methoxy-spiro[imidazolidine-4,1'-3'H-1',2'-dihydronaphthalen-4'-one]2,5-dione 2,5-Dioxo-4-m-methoxyphenyl-4-imidazolidinepropionic acid (8.35 g, 30 mmol) was combined with 60 ml polyphosphoric acid at 150° C. for 1 hour. The reaction mixture was cooled to 25° C. and diluted with water. The resultant solid was collected by filtration and was decolorized with activated charcoal in an aqueous solution and crystallized from water to give 2.9 g (37% yield) of the title compound: mp 250°–251° C.

Anal. Calcd for $C_{13}H_{12}N_2O_4$: C, 60.00; H, 4.65; N, 10.76. Found: C, 59.83; H, 4.71; N, 10.79.

EXAMPLE 14

7'-Nitro-spiro[imidazolidine-4,1'-3'H-1',2'-dihydronaphthalen-4'-one]2,5-dione

The procedure of Example 11 is employed to prepare the title compound of the instant example with 2,5-dioxo-4-m-nitrophenyl-4-imidazolidinepropionic acid as the starting material substituted for the m-fluorophenyl compound.

EXAMPLE 15

7'-Chloro-6'-methyl-spiro[imidazolidine-4,1'-3'H-1',2'-dihydronaphthalen-4'-one]2,5-dione 4-(m-Chloro-p-methylphenyl)-2,5-dioxo-4-imidazolidinepropionic acid (10.0 g, 34 mmol) was combined with 150 ml concentrated sulfuric acid and heated at 80° C. for 2 hours. The reaction mixture was cooled to 25° C. and poured onto ice. The resulting white solid was collected and washed with water and dried to give 8.78 g (94% yield) of crude product: mp 260°–265° C. The crude product was recrystallized from isopropanol-water to give 5.80 g of the title compound: mp 277°–278° C.

Anal. Calcd. for $C_{13}H_{11}N_2O_3Cl$: C, 56.03; H, 3.98; N, 10.05. Found: C, 55.63; H, 4.01; N, 9.96.

EXAMPLE 16

6'-Methyl-spiro[imidazolidine-4,1'-3'H-1', 2'-dihydronaphthalen-4'-one]2,5-dione 2,5-Dioxo-4-p-tolyl-4-imidazolidinepropionic acid (Chem. Abstr. Reg. No. 30741-74-3) (2.85 g, 10.9 mmol) was combined with 25 ml concentrated sulfuric acid and heated at 95° C. for 1.5 hours. The reaction mixture was poured onto ice and the resultant solid was collected by filtration, washed with water and dried to give 1.88 g (71% yield) of crude product: mp 206°–214° C. The crude material (1.76 g) was recrystallized from isopropanol to give 1.12 g of the title compound: mp 245°–248° C.

Anal. Calcd. for $C_{13}H_{12}N_2O_3$: C, 63.93; H, 4.95; N, 11.47. Found: C, 63.56; H, 5.15; N, 11.24.

EXAMPLE 17

7'-Chloro-spiro[imidazolidine-4,1'-3'H-1',2'-dihydronaphthalen-4'-one]2,5-dione 2,5-Dioxo-4-(m-chlorophenyl)-4-imidazolidinepropionic acid (5.42 g, 20.0 mmol) was combined with 40 ml concentrated sulfuric acid, heated at 90° C. for 3 hours and then cooled to 25° C. and poured onto ice. The resultant solid was collected, dried and recrystallized from water to give 2.61 g of material, mp 202°–230° C. NMR analysis indicated that this material was a mixture of the starting propionic acid and the desired product. Accordingly, 2.4 g of this material was combined with 25 ml concentrated sulfuric acid and heated at 120° C. for 3 hours. The reaction was cooled to 25° C., poured onto ice and the resultant solid collected by filtration and recrystallized from water to give 700 mg (14% yield) of the title compound: mp 279°–280° C.

Anal. Calcd. for $C_{12}H_9N_2O_3Cl$: C, 54.58; H, 3.41; N, 10.60. Found: C, 54.42; H, 3.60; N, 10.42.

EXAMPLE 18

3'-Methyl-7'-fluoro-spiro[imidazolidine-4,1'-3'H-1',2'dihydronaphthalen-4'-one]2,5-dione 2,5-Dioxo-4-m-fluorophenyl-4-imidazolidineisobutyric acid (2.1 g, 7.5 mmol) was combined with 30 ml concentrated sulfuric acid and heated at 115°–120° C. for 2 hours. The reaction mixture was poured onto ice and the quenched reaction mixture was stirred with activated charcoal for 30 minutes. The reaction mixture was filtered through a diatomaceous earth filter and the filter pad was taken up in 250 ml methanol at reflux and refiltered. The residue was extracted again with 250 ml methanol at reflux and filtered. The combined filtrates were concentrated in vacuo to a gum. The gum was stirred in water for 3 hours and the resulting white solid was collected by filtration and dried to give 0.85 g (43% yield) of the title compound: mp 216°–220° C. An analytical sample was prepared by crystallization from water: mp 224°–225° C.

Anal. Calcd for $C_{13}H_{11}FN_2O_3$: C, 59.54; H, 4.23; N, 10.68. Found: C, 59.41; H, 4.32; N, 10.71.

NMR (DMSO-$d_6$, 250 MHz) showed a diasteromeric pair in the ratio of 94:6; major component: δ 11.07 (bs, 1H), 8.60 (s, 1H), 8.05 (m,1H) 7.39 (m, 1H), 7.24 (m, 1H), 3.34 (m, 1H), 2.5 (t, 1H), 2.18 (t, 1H) and 1.15 (d, 3H) ppm; minor component: δ 8.94 (s, 1H), 3.0 (m, 1H) and 1.18 (d, 3H) ppm.

Separation of Diastereomers

A crude sample of 94.0 g of 3'-methyl-7'-fluorospiro[imidazolidine-4,1'-3'H-1',2'-dihydronaphthalen-4'one]2,5-dione was isolated according to the general procedure described above. Nuclear magnetic resonance analysis showed that the crude sample consisted of three components: 5.85 mol percent of racemic 4,1'(S)-3'(S)-Spiro[imidazolidine-4,1'(2'H)-3'H-naphthalen-4'-one]-2,5-dione-3'-methyl-7-fluoro; 71.70 mol percent of the related 4,1'(S)-3'(R) epimer and 22.44 mol percent of uncyclized precursor carboxylic acid.

This mixture was slurried in 1.5 liters of acetonitrile at reflux and 300 ml of methanol was added to obtain a solution. Following decolorization with activated charcoal the solution was concentrated to 800 ml by boiling off solvent. A solid (13.04 g) formed which was filtered off. The mother liquors were concentrated in vacuo to a solid which was redissolved in acetonitrile and concentrated to 300 ml by boiling off solvent. A solid (39.44 g) formed in the concentrate and was filtered off. On standing the mother liquors deposited an additional 1.17 g of solid which were removed by filtration. The mother liquors were concentrated in vacuo to a glassy foam. Chloroform was added and on stirring overnight 9.0 g of solid formed and was removed by filtration. The mother liquors were concentrated in vacuo to a wet foam (25 to 30 g).

This foam was placed on a column of silica gel (230–400 mesh) and eluted with 5 percent methanol in chloroform to give 6.77 g of material consisting of only two components: Nuclear magnetic resonance analysis showed that this material was now enriched in racemic 4,1'(S)-3'(S)-spiro[imidazolidine-4,1'(2H)-3'H-naphtha-lene-4'-one]2,5-dione-3'-methyl-7-fluoro to the extent of 58.3 mol percent. The other component of 41.7 mol percent consisted of the corresponding racemic 4,1'(S)-3'(R) epimer.

Using a Zorbax-Sil preparative high pressure liquid chromatography column and a programmed 5 to 20 percent isopropyl alcohol-hexane gradient six samples of 250 mg of the 58.3 to 41.7 diastereomeric mixture were chromatographed and the peak with shorter retention time was isolated. Combining similar fractions of the shorter retention time peak gave 369 mg of material melting point 196°–199° C. Reanalysis of this material by high pressure liquid chromatography showed a major peak with area percent 97.449 and retention time 5.78 minutes and two minor peaks with area percent 2.23 and retention time 6.33 minutes and area percent 0.32 and retention time 6.76 minutes. By nuclear magnetic resonance analysis the material with retention time 5.78 minutes is identified as the racemic rel 4,1'(S)-3'(S)-spiro[imidazolidine-4,1'(2'H)-3'H-naphthalen-4'-one]2,5-dione-3'-methyl-7'-fluoro, the minor epimer found in the product described above.

The major epimer in the product described above is the racemic rel 4,1'(S)-3'(R)-spiro[imidazolidine-4,1'(2'H)-3'H-naphthalen-4'-one]2,5-dione-3'-methyl-7'-fluoro which can be isolated in greater than 99 mol percent purity by repeated crystallization from acetonitrile. Using this procedure the 4,1'(S)-3'(R) epimer has melting point 230°–232° C. and retention time 6.34 minutes.

EXAMPLE 19

(+) 7'-Fluoro-spiro[imidazolidine-4,1'-3'H-1',2'-dihydronaphthalen-4'-one]2,5-dione (±)7'-Fluoro-spiro[imidazolidine-4,1'-3'H-1',2'-dihydro-naphthalen-4'-one]2,5-dione (24.62 g, 0.099 mol) was dissolved in 700 ml of refluxing acetonitrile. To this solution was added 42.96 g (0.0998 mol) of brucine dihydrate. The acetonitrile mixture was filtered while hot to remove traces of insoluble material and the filtrate was allowed to cool to 25° C. The resultant solid was collected by filtration and dried to give 26.83 g of a salt: mp 229°–230° C., with decomposition; $[\alpha]_D^{20}$ +30.7° (methanol). This salt was recrystallized from acetonitrile to give 18.8 g of a purified salt: mp 230° C., with decomposition; $[\alpha]_D^{20}$ +32.0° C. (methanol).

The purified salt (17.8 g) was decomposed by stirring with 500 ml chloroform. Initially most of the salt dissolved and then a new solid formed. This new solid was collected by filtration and dried to give 6.32 g of the title compound: mp 263°–264° C.; $[\alpha]_D^{20}$ +203.5° (methanol).

The absolute configuration at the 4,1' center is assigned as "S" based on single crystal X-ray analysis.

EXAMPLE 20

3'-Bromo-7'-fluoro-spiro[imidazolidine-4,1'-3'H-1',2'-dihydronaphthalen-4'-one]2,5-dione 7'-Fluoro-spiro[imidazolidine-4,1'-3'H-1',2'-dihydro-naphthalen-4'-one]2,5-dione (1.6 g, 6.4 mmol) was combined with 1.13 g (7.1 mmol) bromine and 1 ml concentrated hydrobromic acid in 15 ml glacial acetic acid and heated at 80° C. for 10 min at which time the bromine color disappeared. The reaction was concentrated in vacuo to a white solid by filtration and dried to give 1.9 g (91%) of the title compound: mp 223°–224° C.

Anal. Calcd. for $C_{12}H_8N_2O_3BrF$: C, 44.06; H, 2.47; N, 8.56. Found: C, 43.61; H, 2.61; N, 8.31.

EXAMPLE 21

7'-Methyl-spiro[imidazolidine-(4,1')-3'H-1',2'-dihydronaphthalene-4'-one]2,5-dione 2,5-Dioxo-4-m-tolyl-4-imidazolidinepropionic acid (1.4 g, 5.3 mmol) was combined with 25 ml concentrated sulfuric acid and heated at 95° C. for 30 minutes. The reaction mixture was poured onto ice and the resultant solid was collected by filtration and decolorized with DARCO G-60 activated charcoal (available from ICI Americas Inc.) in hot water and was crystallized from water to give 420 mg (32% yield) of the title compound: mp 206° C.

Anal. Calcd for $C_{13}H_{12}N_2O_3$: C, 63.93; H, 4.95; N, 11.47. Found: C, 63.57; H, 4.91; N, 11.45.

The spent carbon black was dried and extracted with methanol at reflux to give an additional 110 mg (8.5% yield) of the title product: mp 202° C.

EXAMPLE 22

5',7'-Dimethyl-spiro[imidazolidine-4,1'-3'H-1',2'-dihydronaphthalen-4'-one]2,5-dione 2,5-Dioxo-4-m-xylyl-4-imidazolidinepropionic acid (1.0 g, 3.7 mmol) was combined with 20 ml concentrated sulfuric acid and heated at 85° C. for 45 minutes, cooled to 25° C. and poured onto ice. The resultant tan precipitate was collected by filtration, dried, dissolved in 200 ml methanol at reflux and decolorized with DARCO G60 activated charcoal. The methanol solution was conconcentrated in vacuo, and the residue was triturated with 10 ml water. The resultant solid was collected by filtration and dried to give 630 mg (70% yield) of the title compound: mp 260°-261° C.

Anal. Calcd for $C_{14}H_{14}N_2O_3$: C, 65.11; H, 5.46; N, 10.85. Found: C, 64.80; H, 5.48; N, 10.73.

EXAMPLE 23

6'-Chloro-spiro[imidazolidine-4,1'-3'H-1',2'-dihydronaphthalen-4'-one]2,5-dione 2,5-Dioxo-4-p-chlorophenyl-4-imidazolidinepropionic acid (Chem. Abstr. Reg. No. 30741-76-5) (5.0 g, 18 mmol) was combined with 90 ml concentrated sulfuric acid and heated at 115° C. for 16 hours. The reaction was cooled to 25° C. and poured onto 800 g ice and was stirred for 2 hours. DARCO G-60 activated charcoal was added and stirring was continued for 1.5 hours. The reaction was filtred through diatomaceous earth and the filtrate was washed with 400 ml water and then the filtered solid, DARCO G-60 activated charcoal and diatomaceous earth was stirred with 500 ml methanol at reflux. After 30 minutes stirring the slurry was again filtered through diatomaceous earth and the clear material was concentrated in vacuo to give 1.1 g of material which by nmr appeared to be a 1:1 mixture of starting material and the title compound. The 1.1 g was slurried in methanol and filtered to give 0.31 g (6%) of the title compound: mp 258°-261° C. An analytical sample was recrystallized from water to give the title compound: mp 265°-266° C.

Anal. Calcd. for $C_{12}H_9N_2O_3Cl$: C, 54.46; H, 3.43; N, 10.58. Found: C, 54.21; H, 3.41; N, 10.40.

EXAMPLE 24

7'-Fluoro-4'-hydroxy-3'-methyl-spiro[imidazolidine-4,1'-1',2',3',4'-tetrahydronaphthalene]2,5-dione 7'-Fluoro-3'-methyl-spiro[imidazolidine-4,1'-3'H-1',2'-dihydronaphthalen-4'-one]2,5-dione (1.31 g, 5.0 mmol) was slurried in 25 ml methanol at 0° C. and 378 mg (10.0 mmol) sodium borohydride was added. Solution occurred as the reaction proceeded. After gas evolution stopped the reaction was concentrated in vacuo to a solid. This was dissolved in 15 ml water and 6N hydrochloric acid was added until a final pH of 1 was reached. A white solid formed which was collected by filtration, washed with water and dried to give 1.0 g (76% yield) of the title compound: mp 279°-281° C.

Anal. Calcd. for $C_{13}H_{13}N_2O_3F$: C, 59.09; H, 4.96; N, 10.60. Found: C, 58.00; H, 4.93; N, 10.46.

EXAMPLE 25

7'-Fluoro-4'-hydroxy-spiro[imidazolidine-4,1'-1',2',3',4'-tetrahydronaphthalene]2,5-dione 7'-Fluoro-spiro[imidazolidine-4,1'-3'H-1',2'-dihydronaphthalen-4'-one]2,5-dione (2.0 g, 8.1 mmol) was dissolved in 50 ml methanol and cooled to 0° C. Sodium borohydride (0.6 g, 16.0 mmol) was added in small portions over 15 minutes. After stirring at 0° C. for 1 hour the reaction was poured into 10% aqueous hydrochloric acid and methanol was removed at reduced pressure. The resulting solid was collected by filtration and dried and then recrystallized from water to give 0.7 g (35% yield) of the title compound: mp 258°-259° C.

Anal. Calcd. for $C_{12}H_{11}N_2O_3F$: C, 57.59; H, 4.43; N, 11.20. Found: C, 57.70; H, 4.41; N, 11.31.

EXAMPLE 26

(−)7'-Fluoro-spiro[imidazolidine-4,1'-3'H-1',2'-dihydronaphthalen-4'-one]2,5-dione 24.62 (0.099 mol) of (+) 7'-Fluoro-spiro[imidazolidine-4,1'-3'H-1',2'-dihydronaphthalen-4'-one]2,5-dione was dissolved in 700 ml acetonitrile at reflux and to the solution was added 42.96 g (0.104 mol) of brucine hydrate. The acetonitrile was filtered while hot to remove a small amount of insoluble material and was allowed to slowly cool. The resultant crop of crystals was removed from the acetonitrile mother liquors which were concentrated to an oily foam. This material was triturated with ether to give 34.46 g of a tan solid $[\alpha]_D^{25} = -105.4$ (methanol, C=1). The tan solid was dissolved in chloroform. Initially the solid dissolved but within a short time a new solid began to form. This was collected by filtration to give 8.2 g : mp 258°-260° C. Trituration with 500 ml hot chloroform followed by filtration and drying gave 7.54 g of a solid: mp 260°-262° C. A portion of this solid material was washed with 0.1N hydrochloric acid and dried and recrystallized from hot methanol to give (−)7'-Fluoro-spiro[imidazolidine-4,1'-3'H-1',2'-dihydronaphthalen-4'-one]2,5-dione: mp 264°-265° C. $[\alpha]_D^{25} = -197.9°$ (methanol, C=1).

EXAMPLE 27

(+) 7'-Fluoro-4'-hydroxy-3'-methyl-spiro[imidazolidine-4,1'-1',2', 3',4'-tetrahydronaphthalene]2,5-dione 99.51 g (0.379 mol) of (±)7'-Fluoro-4'-hydroxy-3'-methyl-spiro[imidazolidine-4,1'-1',2',3',4'-tetrahydronaphthalene]2,5-dione was combined with 171.0 g (0.398 mol) brucine dihydrate and was dissolved in 1.4 liter ethanol at reflux. The ethanol was filtered while hot to remove a small amount of insoluble material and was concentrated in vacuo to a foam. This foam was combined with 3.0 liters of acetonitrile at reflux. Some solid formed during this procedure. The reaction was allowed to cool to 23° C. The resultant solid was collected by filtration to give 128.96 g of solid: mp 222°-224° C.; $[\alpha]_D^{25} = -6.4°$ (methanol, C=1). In a similar manner from 20.34 g of the racemic alcohol was isolated 24.82 g of the brucine salt: mp 224°-226° C.; $[\alpha]_D^{25} = -5.8$ (methanol, C=1). The combined salts (153.78 g) were added to 1.5 liters of acetonitrile at reflux; 200 ml acetonitrile were boiled off and the reaction was allowed to cool to 23° C. over 20 hours. The resulting solid was removed by filtration and dried dried to give 137.63 g: mp 226°-227° C.; $[\alpha]_D^{25} = 3.6°$ (methanol, C=1). This material was slurried in 1 liter boiling acetonitrile and allowed to cool to 23° C. and the resulting solid was collected by filtration and dried to give 128.63 g: mp 227°-228° C.; $[\alpha]_D^{25} = +5.0°$ (methanol, C=1). The salt components were separated by slurrying in 1 liter of chloroform at 23° C. for 1 hr. and then allowing the mixture to remain at 23° C. for 20 hours. The resultant solid was collected by filtration and dried to give 45.45 g of the title compound: mp 257.5°-258.5° C.; $[\alpha]_D^{25} = +120.1°$ (methanol, C=1).

The absolute configuration at the 4,1', 3' and 4' centers are assigned as 4,1'S, 3'R and 4'S based on a combination of single crystal X-ray, nuclear magnetic resonance and chemical interconversion studies.

EXAMPLE 28

(+)7'-Fluoro-3'-methyl-spiro[imidazolidine-4,1'-3'H-1',2'-dihydronaphthalene-4'-one]2,5-dione 40.45 g (0.153 mol) of (+)7'-Fluoro-4'-hydroxy-3'-methyl-spiro[imidazolidine-4,1'-1',2',3',4'-tetrahydronaphthalene]2,5-dione was combined with 15.31 g (0.153 mol) chromium trioxide in 250 ml glacial acetic acid and the reaction temperature was maintained at 25° C. After 1.5 hours the reaction was concentrated in vacuo to a crude solid. This solid was triturated with 150 ml water and the resultant solid was collected by filtration and washed with two 125 ml portions of water. After drying this material was recrystallized from acetonitrile after decolorization with DARGO G-60 activated charcoal to give 25.05 g of the title compound: mp 250°-251° C.; $[\alpha]_D^{25} = +231.1°$ (methanol, C=1).

Anal. Calcd. for $C_{13}H_{11}N_2O_3F$: C, 59.54; H, 4.23; N, 10.68. Found: C, 59.36; H, 4.38; N, 10.70.

The absolute configurations at the 4,1' and 3' centers are assigned as "S" and "R", respectively, based on single crystal X-ray analysis.

EXAMPLE 29

(−)
7'-Fluoro-4'-hydroxy-3'-methyl-spiro[imidazolidine-4,1'-1',2',3',4'-tetrahydronaphthalene]2,5-dione The acetonitrile mother liquors remaining after removal of 137.63 g of solid mp 226°-227° C. (Example 27); $[\alpha]_D^{25} = +3.6°$ C. (CH₃OH, C=1) were concentrated in vacuo to a foam. This foam was stirred with 1 liter of chloroform and a solid formed and was collected by filtration and washed thoroughly with five 1 liter portions chloroform and dried to give 48.22 g of the title compound: mp 253°-254° C. with decomposition; $[\alpha]_D^{25} = -114.2°$ (CH₃OH, C=1).

EXAMPLE 30

(−)
7'-Fluoro-3'-methyl-spiro[imidazolidine-4,1'-3'H-1',2'-dihydronaphthalene-4-one]2,5-dione 39.6 g (0.15 mol) of (−) 7'-Fluoro-4'-hydroxy-3'-methyl-spiro[imidazolidine-4,1'-1',2',3',4'-tetrahydronaphthalene]2,5-dione was combined with 15.0 g (0.15 mol) of chromium trioxide in 200 ml of glacial acetic acid and stirred at 25° C. with some cooling required until the initial, exotherm ceased. After 2 hours, thin layer chromatographic analysis showed the reaction was essentially complete. The reaction was concentrated in vacuo to a dark solid which was triturated with water and the solid collected by filtration. The solid was washed with water until the wash was colorless and then dried to give 36.82 g of crude product. This product was recrystallized from acetonitrile after being decolorized with activated charcoal admixed with diatomaceous earth to give the title compound as a white crystalline solid amounting to 21.50 g; mp=149°-150.5° C. with decompostion; $[\alpha]_D^{25} = -223.4°$ (CH₃OH, C=1).

EXAMPLE 31

(±)
7'-Fluoro-3'-methyl-spiro[imidazolidine-4,1'-3,H-1',2'-dihydronaphthalene-4-one]2,5-dione 97.4 g of crude 3'-methyl-7'-fluoro-spiro[imidazolidine-4,1'-3'H -1',2'-dihydronaphthalen-4'-one]2,5-dione was prepared according to the general procedure described in Example 18. Nuclear magnetic resonance studies showed that this crude product contained 2,5-dioxo-4-(m-fluorophenyl)-4-imidazolidinepropionic acid and two dihydronaphthalen-4-one products. High pressure liquid chromatographic analysis (5-20% isopropanol-hexane gradient, 10 min. seg length, 2 ml/min flow on a Zorbax-Sil column using a Dupont Series 8800 instrument) indicated that the earlier eluting minor dihydronaphthalen-4-one component amounted to 9.44% by peak area (254 nm detector) of the peaks attributable to dihydronaphthalen-4-one products. 94.0 g of the crude sample was slurried in 1.5 liter acetonitrile at reflux. Methanol was added until solution occurred. The solution was decolorized with activated charcoal admixed with diatomaceous earth, filtered and concentrated by boiling off solvent to 800 ml at which point a solid formed and was removed by filtration and dried to give 13.04 g; mp=247°-251° C. of 4-(m-chlorophenyl)-4-imidazol-idinepropionic acid. The acetonitrile-methanol mother liquors were concentrated in vacuo and redisolved in acetonitrile and concentrated by boiling to 300 ml. A solid amounting to 39.44 g; mp: 222°-227° C., formed and was removed by filtration. Upon standing at 25° C. for 2 days an additional 1.17 g of solid, mp 208°-212° C., was removed by filtration. The mother liquors were concentrated in vacuo to a glassy foam. This foam material was stirred with chloroform and a solid formed after overnight stirring and 9.0 g of material was removed; mp: shrinks at 181° C., mp 199°-201° C. with decomposition. The mother liquors were concentrated in vacuo to a foam which weighed about 25-30 g and contained trapped solvent.

This foam material was placed on a column of silica gel (230-400 mesh) and was eluted with 5% methanol in chloroform solvent. Fractions containing dihydronaphthalen-4-one products were collected and concentrated in vacuo to give 6.77 g of material whose composition as determined by nuclear magnetic resonance analysis was a 58.3: 41.7 mol percent mixture of two diastereomers. This material was analyzed by high pressure liquid chromatography and the earlier eluting peak exhibited peak area 57.18 compared to a later eluting peak with area 42.82 in agreement with the nuclear magnetic resonance analysis.

The analyzed concentrated fractions (1.5 g) were subjected to preparative high pressure liquid chromatographic separation in six injections on a preparative Zorbax-Sil column (5–20% isopropanol-hexane gradient, 40 ml/min flow, detector at 300 nm). The earlier eluting major peak fractions were collected and concentrated in vacuo to give 369 mg of solid; mp: 196°–199° C. Anal. Calcd. for $C_{13}H_{11}O_2N_2F$: C, 59.54; H, 4.23; N, 10.68. Found: C, 59.22; H, 4.29; N, 10.53. High pressure liquid chromatographic analysis indicated that this material had been enriched in the earlier eluting diastereomer. By peak area, sample composition was 97.49% earlier eluting diastereomer, 2.23% of a later eluting unidentified minor product. Based on a combination of spectral and single crystal X-ray analysis the structure of the 97.49% racemic component is rel 4,1'S, 3'S.

EXAMPLE 32

(±)
7'-Chloro-3',3'-dimethyl-spiro[imidazolidine-4,1'-1',2'-dihydronaphthalen-4-one]2,5-dione 2,5-Dioxo-3,3-dimethyl-4-(m-chlorophenyl)-4-imidazolidinepropionic acid (0.62 g, 2 mmol) was combined with 4 ml concentrated sulfuric acid and heated at 70° C. for 4 hours. The reaction was poured over ice and the solid which formed was collected by filtration, washed with water and dried to give 412 mg of solid. This solid was taken up in hot acetonitrile, decolorized with activated charcoal admixed with diatomaceous earth and the white solid that formed on cooling was collected by filtration and dried to give 140 mg, of the title compound; mp: 264°–266° C. Anal. Calcd for $C_{13}H_{11}O_3N_2F$: C,57.44; H, 4.48; N, 9.57. Found: C, 57.26; H, 4.51; N, 9.63.

EXAMPLE 33

(±)
3',3'-Dimethyl-spiro[imidazolidine-4,1'-1',2'-dihydronaphthalen-4'-one]2,5-dione 2,5-Dioxo-3,3-dimethyl-4-phenyl-4-imidazolidinepropionic acid (26.94 g, 0.1 mol) was combined with 135 ml of concentrated sulfuric acid and heated at 70° C. for 5 hours and then poured over ice. A solid formed which was collected by filtration and dried to give 21.04 g of crude product. The crude product (19.35 g) was dissolved in 150 ml 1N sodium hydroxide and was decolorized with activated carbon admixed with diatomaceous earth. The basic solution was brought to pH 7 with hydrochloric acid and the resultant solid was collected by filtration and washed twice with water. This procedure was repeated again and the resultant solid was partitioned between 75 ml dilute hydrochloric acid and 400 ml ethyl acetate. The ethyl acetate layer was washed with brine, dried over anhydrous sodium sulfate and concentrated to give 12.54 g of the title compound; mp: 229°–231° C. Anal. Calcd for $C_{14}H_{14}O_3N_2$: C, 65.10; H, 5.46; N, 10.85. Found: C, 64.74; H, 5.53; N, 10.74.

EXAMPLE 34

(±)
7'-Chloro-3'-methyl-spiro[imidazolidine-4,1'-3'H-1',2'-dihydronaphthalen-4-'-one]2,5-dione 2,5-Dioxo-3-methyl-4-(m-chlorophenyl)-4-imidazolidinepropionic acid (10.72 g, 36.1 mmol) was combined with 55 ml of concentrated sulfuric acid and heated at 70° C. for 5 hours. The reaction mixture was poured onto ice water and the resultant solid was collected by filtration, washed with water and dried to give 7.96 g of crude product. The crude product (7.76 g) was dissolved in 400 ml boiling acetonitrile and was decolorized with activated charcoal, filtered and allowed to cool to 25° C. The resulting solid was collected by filtration and dried to give 4.48 g of the title compound; m.p. 232°–234° C. partial melt, 255°–257° C., decomposition Anal. Calcd for $C_{13}H_{11}O_3N_2C$: C, 56.02; H, 3.98; N, 10.05. Found: C, 56.17; H, 4.08; N, 10.13.

EXAMPLE 35

(+)
7'-Fluoro-3'-benzyl-spiro[imidazolidine-4,1'-3'H-1',2'-dihydronaphthalen-4'-one]2,5-dione (+)7'-Fluoro-3'-benzylidene-spiro[imidazolidine-4,1'-1'2'-dihydronaphthalen-4'-one]2,5-dione (1.02 g, 3.16 mmol) dissolved in 100 ml ethanol was hydrogenated using 100 mg 5% palladium on carbon at atmospheric pressure and room temperature for 1.5 hours. The catalyst was removed by filtration and the ethanol removed in vacuo to afford a crude product, which was recrystallized from isopropanol to give 794 mg of the title compound as a mixture of diastereomers.

The minor diastereomer could be isolated by the following procedure. The mixture (794 mg) was contacted with 0.656 ml triethylamine in 60 ml ethanol for three days and then concentrated in vacuo to give a solid which was recrystallized from acetonitrile to yield 330 mg of solid. The mother liquors were concentrated in vacuo and the residue was again recrystallized to yield 130 mg of solid, and the resulting mother liquors were concentrated in vacuo and recrystallized from ethanol to give a solid which after washing with diethyl ether and drying gave 33 mg of minor diastereomer; mp: 225°–226° C. $[\alpha]_D^{25} = 120°$ ($CH_3OH$, c=1). High resolution mass spectrum: calcd. for $C_{19}H_{15}N_2O_3F$: 338.1067. Found: 338.1067.

The major diastereomer could be isolated as follows. Using 672 mg (2 mmol) of (+) 7'-fluoro-3'-benzylidene-spiro[imidazolidine-4',1'-1',2'-dihydronaphathalen-4'-one]2,5-dione and using the hydrogenation conditions described above there was isolated a crude product consisting of predominantly one diastereomer. Recrystallization from isopropanol gave 460 mg of the major diastereomer; mp: 238°–240° C. $[\alpha]_D^{25} = -31°$ ($CH_3OH$, c=1).

EXAMPLE 36

(±)
7-Fluoro-3-methylspiro[3,4-dihydronaphthalen-1(2H), 5'-oxazolidine]2', 4, 4'-trione The title compound is named using chemical abstracts nomenclature and corresponds to the compound of formula Ib in which U is oxygen, X is methyl, W is carbonyl, Y is fluoro and Z is hydrogen.

(±) 7-Fluoro-3-methylspiro[3,4-dihydronaphthalene-1(2H), 5'-oxazolidine]2',4'-dione (100 mg, 0.4 mmol) was combined with 106 microliters (0.4 mmol) of bis(-trimethylsilyl)-trifluoroacetamide in 5 ml chloroform. To this reaction mixture was added 0.06 g (0.375 mmol) of bromine in 5 ml chloroform and the solution was stirred at 25° C. for 20 hours at which time a solid was observed on the flask walls and the reaction solvent color had changed from amber to pale yellow. The reaction was concentrated in vacuo and 10 ml water was added with little or no noticeable solubility of the oily bromination product. Tetrahydrofuran was added until a clear solution was obtained and the reaction was stirred at 25° C. for 6 hours. During this time the reaction pH gradually approached 2.5. For an additional 18 hours the reaction was warmed at 50° C. and then worked-up by removing tetrahydrofuran in vacuo, adding 20 ml water and partitioning between methylene chloride and water. The organic phase was washed with brine, dried over anhydrous sodium sulfate and the solvent removed to give 40 mg of crude solvolysis product. This product was dissolved in 5 ml ethyl acetate and 1 ml glacial acetic acid. To this solution was added 180 mg (0.4 mmol) of chromium trioxide and the resulting green solution was stirred at 25° C. for 2.5 hours. Thin layer chromatographic analysis (silica gel-ethyl acetate eluent) showed a new spot rf=0.66 with strong short wavelength (254 nm) ultraviolet absorbance. The reaction mixture was worked-up by adding 20 ml ethyl acetate and washing the green organic solution with three 20 ml portions of an oxalic acid solution (0.76 g oxalic acid in 60 ml water). The ethylacetate layer was washed with brine, dried over anhydrous sodium sulfate and the solvent removed in vacuo to give 48.25 mg of a brown gummy solid which when exposed to high vacuum turned to a foam of the title compound. High resolution mass spectrum calcd for $C_{13}H_{10}NO_4F$: 263.0594. Found: 263.0572. The infrared spectrum of a chloroform solution of the foam had absorptions at 1820, 1750, and 1690 cm$^{-1}$.

In a similar procedure 3.01 g (12.09 mmol) of (+) 7-fluoro-3-methylspiro[3,4-dihydronaphthalene-1(2H), 5'-oxazolidine]2',4'-dione as a 2:1 ratio of diastereomers was converted to 1.24 g of crude title product. This product was subjected to partial purification by chromatography on silica gel using 10% isopropanol-hexane as eluent followed by preparative high pressure liquid chromatographic purification on a Zorbax C-8 column using 5% methanol in methylene chloride as solvent to give 262 mg of a pale yellow foam. 250 MHz nuclear magnetic resonance analysis (deuterochloroform solvent) showed two diastereomers in a 69:31 ratio. The major diastereomer showed an aromatic multiplet at 7.04–7.18 ppm. and methine hydrogen multiplet at 3.34–3.53 ppm. The minor diastereomer showed an aromatic multiplet at 6.90–6.96 ppm. and methine hydrogen multiplet at 3.05–3.22 ppm. The structure of the major diastereomer is assigned as Rel 1,5'S, 3R 7-fluoro-3-methylspiro[3,4-dihydro-naphthalen-1(2H), 5'-oxazolidine]2',4,4'-trione.

EXAMPLE 37

Compounds of formula I of Examples 1–36 were tested for their ability to reduce or inhibit aldose reductase enzyme activity, following the procedure described in U.S. Pat. No. 3,821,383 and based on the procedure of Hayman et al., Journal of Biological Chemistry, 240, 877 (1965). Where the same compound is made by more than one method, the results of the tested compounds are identical regardless of how made. The substrate employed was partially purified aldose reductase enzyme obtained from human placenta. The compounds were tested at levels of to $10^{-4}$ to $10^{-9}$M and were found to inhibit enzyme activity relative to untreated controls.

PREPARATION A 2,5-Dioxo-4-m-fluorophenyl-4-imidazolinepropionic acid m-Fluorobenzene-gamma-oxo-butanoic acid (1.57 g, 8 mmol) (Eur. J. Med. Chem., 13,533 (1978)) was combined with 7.7 g (80 mmol) ammonium carbonate, 1.04 g (16 mmol) potassuum cyanide in 60 ml water and was heated at 70° C. for 20 hours. The reaction mixture was cooled to 25° C. and the acidity adjusted to pH 2 with concentrated hydrochloric acid. The resultant light yellow solid was isolated by filtration and dried in vacuo at 100° C. to give 1.8 g (85% yield) of the title compound mp 206°–208° C. NMR (DMSO-d$_6$):11.08 (bs, 1H), 8.86 (bs, 1H), 7.67–6.83 (m,4H) and 2.25 (bs,4H) ppm.

PREPARATION B 2,5-Dioxo-4-m-methoxyphenyl-4-imidazolidinepropionic acid m-Methoxybenzene-gamma-oxo-butanoic acid (C.A. reg. no. 38102-67-9) (10.0 g, 48 mmol) was combined with 22.75 g (235 mmol) ammonium carbonate, 6.5 g (100 mmol) potassium cyanide in 100 ml ethanol and 100 ml water at 65° C. After 5 hours at 65° C. an additional 22.75 g (235 mmol) ammonium carbonate was added and heating was continued for 18 hours. The reaction mixture was concentrated in vacuo, triturated with water and the acidity was adjusted to pH 4 with concentrated hydrochloric acid. A white solid formed which was collected by filtration and dried in vacuo at 80° C. for 20 hours to give 10.6 g (79% yield) of the title compound: mp 138° C.

Anal. Calcd for $C_{13}H_{14}N_2O_5$: C, 56.11; H, 5.07; N, 10.07. Found: C, 55.46; H, 5.02; N,10.02.

PREPARATION C 2,5-Dioxo-4-m-nitrophenyl-4-imidazolidinepropionic acid

The procedure of Preparation A is employed to prepare the title compound. The starting material is 3-nitrobenzene-gamma-oxo-butanoic acid rather than the 3-fluorobenzene compound.

PREPARATION D 2,5-Dioxo-4-(m-chloro-p-methylphenyl)-4-imidazolidinepropionic acid m-Chloro-p-methylbenzene-gamma-oxo-butanoic acid (22.7 g, 100 mmol) (Bull. Chem. Soc. Jap., 52, 2441–42 (1979)) was combined with 90 g (0.94 mol) ammonium carbonate and 13.7 g (210 mmol) potassium cyanide in 300 ml water and heated at 65° C. for 22 hours. The reaction mixture was cooled to 25° C. and the resulting solid was collected by filtration and suspended in 200 ml water. The aqueous suspension was brought to pH 2 with concentrated hydrochloric acid and the resultant solid was collected by filtration, washed with water and dried to give 27.8 g (94%) of the title compound, mp 196°–199° C.

PREPARATION E

2,5-Dioxo-4-(m-chlorophenyl)-4-imidazolidinepropionic acid

3-Chloro-benzene-gamma-oxo-butanoic acid (Chem. Abstr. Reg. No. 62903-14-4) (10.6 g, 50 mmol) was combined with 47.2 g (490 mmol) ammonium carbonate and 6.5 g (100 mmol) potassium cyanide in 100 ml water and heated at 65° C. for 65 hours. The reaction mixture was cooled to 0° C. The resultant precipitate was collected by filtration and stirred in 100 ml water. Concentrated hydrochloric acid was added to adjust the aqueous pH to 0.5 and the resultant solid was collected by filtration, washed with 300 ml water and dried to give 11.47 g (84% yield) of crude title compound: mp 196°–217° C., with decomposition and purple coloration.

PREPARATION F

2,5-Dioxo-4-m-tolyl-4-imidazolidinepropionic acid

3-Methylbenzene-gamma-oxo-butanoic acid (Chem. Abstr. Reg. No. 59618-44-9) (3.0 g, 10 mmol) was combined with 14.0 g (144 mmol) ammonium carbonate and 2.2 g (34 mmol) potassium cyanide in 50 ml water and heated at 65°–70° C. for 22 hours. The reaction mixture was cooled and brought to pH 2 with concentrated hydrochloric acid to precipitate a solid. The solid was collected by filtration, washed with water and dried to give crude product: mp 173°–178° C. This crude product was dissolved in boiling water and an insoluble orange gum was removed by filtration. Concentration of the resulting aqueous solution in vacuo gave 1.34 g (32% yield) of the title compound: mp 195°–198° C.

Anal. Calcd. for $C_{13}H_{14}N_2O_4$: C, 59.54; H, 5.38; N, 10.68. Found: C, 59.25; H, 5.30; N, 10.32.

PREPARATION G

2,5-Dioxo-4-m-xylyl-4-imidazolidinepropionic acid 3,5-Dimethylbenzene-gamma-oxo-butanoic acid (Chem. Abstr. Reg. No. 36440-58-1) (3.5 g) was combined with 14 g (146 mmol) ammonium carbonate and 2.2 g (33.8 mmol) potassium cyanide in 50 ml water and was heated at 60° C. for 26 hours. The reaction mixture was cooled to 25° C. and filtered to remove oily material. The pH of the filtrate was adjusted to 3.5 with concentrated hydrochloric acid and the resulting white precipitate was collected by filtration and dried to give 1.0 g (22% yield) of the title compound: mp 232°–234° C.

PREPARATION H

3-(m-Fluorobenzoyl)-2-methylpropionic acid

To 180 ml dry dimethylformamide was added 6.5 g (0.10 mol) powdered potassium cyanide. The well stirred slurry was warmed to 80° C. over 30 minutes and was then cooled to 35° C. A solution of 124.1 g (1.0 mol) of m-fluorobenzaldehyde in 50 ml dimethylformamide was added dropwise over 50 minutes during which time the reaction temperature remained at 30° C. After an additional 30 minutes at ambient temperature 67.1 g (1.0 mol) of methacrylonitrile dissolved in 50 ml dimethylformamide was added over 20 minutes. After 3 hours at ambient temperature the reaction was filtered and poured onto 1500 ml water and the oily organic layer was separated. Saturated brine solution was added to the aqueous layer which was then extracted with 3×150 ml chloroform. The combined organic portions were washed consecutively with dilute sulfuric acid, dilute aqueous sodium bicarbonate solution and water. After drying over anhydrous sodium sulfate, the chloroform was removed in vacuo at a temperature not exceeding 35° C. to give 199.8 g of crude oil. To the oil was added 200 ml of concentrated hydrochloric acid and the reaction was heated at 125° C. for 3 hours. The reaction was cooled to 60° C. and the supernatant hydrochloric acid was decanted from a heavier red oil which solidified as it cooled. The red oil/solid was dissolved in 500 ml 3N sodium hydroxide and the aqueous layer was extracted with 4×250 ml diethyl ether. Following cooling in an ice-bath, the aqueous layer was brought to pH 2 with concentrated hydrochloric acid to precipitate a pale-pink solid. This was collected by filtration and dried to give 84.4 g (40% yield) of 3-(m-fluorobenzoyl)-2-methyl-propionic acid: mp 90°–91° C.

PREPARATION I

2,5-Dioxo-3,3-dimethyl-4-(m-chlorophenyl)-4-imidazolidinepropionic acid.

3-(m-Chlorobenzoyl)-2,2-dimethyl-propionic acid (14.4 g, 0.06 mol) was combined with 28.8 g (0.3 mol) ammonium carbonate and 7.81 g (0.12 mol) potassium cyanide in 150 ml water and heated at 70° C. for 24 hours. An additional 5.7 g ammonium carbonate was added and heating at 70° C. was continued for 60 hours. The reaction mixture was cooled in an ice bath and concentrated hydrochloric acid was added dropwise. A tan solid formed, was collected by filtration, washed with water and dried to give 17.34 g of crude product. This material was placed on a column of silica gel and initially eluted with 5% methanol in chloroform and then with 10% methanol in chloroform to give 3.21 g of the title compound as a yellow solid, mp 198°–200° C. with decomposition.

PREPARATION J

3-(m-Chlorobenzoyl)-2,2-dimethylpropionic acid

Using the procedure of T. Joyima et al., *Bull. Chem. Soc. Jap.*, 52(8) 2441–2442 (1979), 3-benzoyl-2,2-dimethylpropionic acid was converted into the title compound by chlorination in the presence of excess aluminum chloride.

PREPARATION K

2,5-Dioxo-3-methyl-4-(m-chlorophenyl)-4-imidazolidine-propionic acid.

3-(m-Chlorobenzoyl)-2-methylpropionic acid (10.36 g, 0.046 mol) was combined with 24.02 g (0.25 mol) ammonium carbonate and 6.5 g (0.10 mol) potassium cyanide in 150 ml water and heated at 70° C. for 23 hours. The reaction mixture was cooled to 20° C. and acidified with concentrated hydrochloric acid. A gummy solid formed which was collected and dissolved in diethyl ether and the diethyl ether solution was washed with 25 ml water. The diethyl ether layer was concentrated in vacuo to a white-yellow solid which was dried overnight at 70° C. in a vacuum oven to give 11.28 g of 2,5-dioxo-3-methyl-4-(m-chlorophenyl-4-imidazolidinepropionic acid; mp 183°–185° C. partial melt, 198°–200° C. decomposition.

PREPARATION L

3-(m-Chlorobenzoyl)-2-methylpropionic acid

Sodium cyanide (1.47 g, 30 mmol) was combined with 100 ml N,N-dimethylformamide and then stirred at 35° C. for 1 hour under nitrogen to give a clear solution. To this solution was added dropwise over 1 hour 34.0 ml (0.3 mol) of 3-chlorobenzaldehyde dissolved in 50 ml N,N-dimethylformamide. After stirring an additional 1 hour at 35° C. a solution of 25.0 ml (0.3 mol) methacrylonitrile in 50 ml N,N-dimethylformamide was added dropwise over 2 hours and the reaction mixture was stirred at 25° C. for 16 hours. Methylene chloride (200 ml) and 4.0 g diatomaceous earth filter aid was added and the mixture was slurried and filtered. The filtrate was washed consecutively with 500 ml 0.22N hydrochloric acid, two 200 ml portions water, 200 ml 2.5% sodium bicarbonate aqueous solution, 200 ml 1N hydrochloric acid, 200 ml water and 200 ml brine. The methylene chloride layer was dried over anhydrous sodium sulfate and concentrated in vacuo to give 49.65 g of crude 3-(m-chlorobenzoyl)-2-methylpropionitrile as a yellow solid; mp: partial melt at 50° C., melt at 79°–81° C. 15.57 g (0.075 mol) of this product was combined with 25 ml concentrated hydrochloric acid and 25 ml formic acid and heated at reflux for 2.5 hours. After cooling, 150 ml water was added and the aqueous solution was extracted with two 150 ml portions ethyl acetate. The ethyl acetate extract in turn was extracted with two 150 ml portions 20% sodium hydroxide in water. The aqueous extract was acidified with concentrated hydrochloric acid to precipitate a solid which was collected by filtration, washed with water and dried to give 10.86 g 3-(m-chlorobenzoyl)-2-methylpropionic acid: mp 100°–102° C.

PREPARATION M

(±) 7'-Fluoro-3'-benzylidene-spiro[imidazolidine-4,1'-1',2'-dihydronaphthalen-4'-one]2,5-dione (+) 7'-Fluoro-spiro[imidazolidine-4,1'-3'H-1',2'-dihydronaphthalen-4'-one]2,5-dione (1.24 g, 5 mmol) (Example 19) was combined with 531 mg (5 mol) benzaldehyde, 14 ml glacial acetic acid and 2.3 ml concentrated sulfuric acid. The suspension was stirred for 64 hours and a clear solution resulted. The solution was poured into ice water and the resultant solid was collected by filtration, washed with water and dried. A repeat reaction using 2.48 g of the product of Example 19 gave after recrystallization from isopropanol-water (95:5) 1.62 g of (±) 7'-fluoro-3'-benzylidenespiro[imidazolidine-4,1'-1',2'-dihydronaphthalen-4'-one]dione; mp: 290°–292° C., $[\alpha]_D^{25} = 121°$ C. (CH$_3$OH, c=1) Anal. Calcd for C$_{19}$H$_{12}$O$_3$N$_2$ClF: C, 67.85; H, 3.90; N, 8.33. Found: C, 68.07; H, 4.01; N, 8.28.

PREPARATION N

(±) 7-Fluoro-3-methylspiro[3,4-dihydronapthalene-1(2H), 5'-oxazolidine]2',4'-dione The title compound is named using chemical abstracts nomenclature and corresponds to the compound of formula Ib in which U is oxygen, X is methyl, W is methylene, Y is fluoro and Z is hydrogen.

In a 250 ml flask equipped with a nitrogen inlet, thermometer, gas inlet and a gas outlet leading to an efficient trap for phosgene gas was placed 2.51 g (10.0 mmol) of 7-fluoro-1-hydroxy-3-methyl-tetralincarboximidic acid ethyl ester and 2.92 ml (21.0 mmol) of triethylamine in 100 ml dry tetrahydrofuran. The reaction was cooled to 0° C. under nitrogen and then phosgene gas was passed through the tetrahydrofuran by a gas bubbles for 0.5 h. The reaction was allowed to warm to 25° C. and was poured onto 500 ml of crushed ice in a well ventilated hood and the mixture was extracted with two 300 ml methylene chloride. The organic phase was washed with brine, dried over anhydrous sodium sulfate and concentrated in vacuo to give 2.463 g of a brown-black gummy solid. Nuclear magnetic resonance analysis of the solid in deuterochloroform showed the product to be a 2:1 mixture of diastereomers. The major diastereomer exhibited an aromatic multiplet (doublet of doublets) at 6.90–6.96 ppm.; the minor diastereomer exhibited an aromatic multiplet (doublet of doublets) at 6.80–6.87 ppm. This diastereomer mixture was used in Example 36.

A crystalline mixture of diastereomers in 2:1 ratio was obtained by trituration in ether-petroleum ether: mp 155°–163° C. A crystalline mixture containing the diastereomer with aromatic multiplet at 6.80–6.87 ppm in the ratio 9:1 to the diastereomer with multiplet at 6.90–6.96 ppm was obtained by precipitation from diethyl ether upon addition of petroleum ether: mp 167°–171° C.

PREPARATION O

(±) 7-Fluoro-1-hydroxy-3-methyltetralincarboximidic acid ethyl ester

This intermediate was prepared from 7-fluoro-3-methyl-α-tetralone by converting the ketone to the trimethylsilylcyanohydrin and then the α-hydroxy imidate ester according to the procedure described by Rodney C. Schnur, et al., *J. Med. Chem.*, 1982, 25, 1451–54.

I claim:

1. A compound of the formula

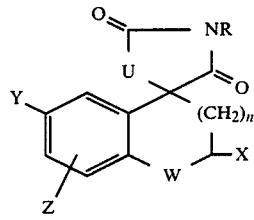

or a pharmaceutically acceptable salt thereof, wherein:
U is oxygen, sulfur or nitrogen substituted with hydrogen or alkyl having 1–4 carbon atoms;
n is zero or one;
W is carbonyl or hydroxymethylene;
R is hydrogen or alkyl having 1–4 carbon atoms;
X is hydrogen, chloro, bromo, iodo, alkyl having 1–4 carbon atoms, dimethy or (CH$_2$)$_m$Q wherein m is 1 or 2 and Q is phenyl or halophenyl, with the proviso that when X is dimethyl, n is one;
Y is hydrogen, halo, nitro, trifluoromethyl, alkoxy having 1–4 carbon atoms or alkyl having 1–4 carbon atoms; and
Z is hydrogen, halo, nitro, trifluoromethyl, alkoxy having 1–4 carbon atoms or alkyl having 1–4 carbon atoms, with the proviso that if either Y or Z is nitro the other is hydrogen.

2. A compound according to claim 1 wherein U is oxygen.

3. A compound according to claim 2 wherein n is one.

4. A compound according to claim 3 wherein W is carbonyl.

5. A compound according to claim 4 wherein R is hydrogen.

6. A compound according to claim 5 wherein X is methyl, Y is fluoro and Z is hydrogen.

7. A compound according to claim 1 wherein U is sulfur.

8. A compound according to claim 1 wherein U is nitrogen substituted with hydrogen.

9. A compound according to claim 8 wherein n is zero.

10. A compound according to claim 9 wherein W is carbonyl.

11. A compound according to claim 10 wherein R is hydrogen.

12. A compound according to claim 11 wherein X, Y and Z are each hydrogen.

13. A compound according to claim 11 wherein X and Z are each hydrogen and Y is fluoro.

14. A compound according to claim 9 wherein W is hydroxymethylene.

15. A compound according to claim 14 wherein R is hydrogen.

16. A compound according to claim 15 wherein X, Y and Z are each hydrogen.

17. A compound according to claim 15 wherein X and Z are each hydrogen and Y is fluoro.

18. A compound according to claim 8 wherein n is one.

19. A compound according to claim 18 wherein W is carbonyl.

20. A compound according to claim 19 wherein R is hydrogen.

21. A compound according to claim 20 wherein X is hydrogen.

22. A compound according to claim 21 wherein Y and Z are hydrogen.

23. A compound according to claim 21 wherein Y is fluoro and Z is hydrogen.

24. A compound according to claim 23 which is the positively rotating enantiomer.

25. A compound according to claim 20 wherein X is bromo.

26. A compound according to claim 25 wherein Y and Z are each hydrogen.

27. A compound according to claim 20 wherein X is methyl.

28. A compound according to claim 27 wherein Y is fluoro and Z is hydrogen.

29. A compound according to claim 28 which is the positively rotating enantiomer.

30. A compound according to claim 20 wherein X is dimethyl.

31. A compound according to claim 30 wherein Y is chloro and Z is hydrogen.

32. A compound according to claim 19 wherein R is alkyl.

33. A compound according to claim 32 wherein R is methyl.

34. A compound according to claim 33 wherein X is methyl.

35. A compound according to claim 34 wherein Z is hydrogen.

36. A compound according to claim 35 wherein Y is fluoro.

37. A compound according to claim 18 wherein W is hydroxymethylene.

38. A compound according to claim 37 wherein R is hydrogen.

39. A compound according to claim 38 wherein X, Y and Z are each hydrogen.

40. A compound according to claim 38 wherein X and Z are hydrogen and Y is fluoro.

41. A compound according to claim 1 wherein U is nitrogen substituted by alkyl.

42. A compound according to claim 41 wherein U is nitrogen substituted by methyl.

43. A compound according to claim 42 wherein n is one.

44. A compound according to claim 43 wherein W is carbonyl.

45. A compound according to claim 44 wherein X is methyl.

46. A compound according to claim 45 wherein Z is hydrogen.

47. A compound according to claim 46 wherein Y is flouoro.

48. A compound according to claim 47 wherein R is alkyl.

49. A compound according to claim 48 wherein R is methyl.

50. A compound according to claim 47 wherein R is hydrogen.

51. A pharmaceutical composition suitable for oral, parenteral or topical administration comprising a pharmaceutically acceptable carrier or diluent and a compound as claimed in claim 1 in an amount effective for the treatment of ocular or neuritic diabetes-associated chronic complications.

52. A composition according to claim 51 wherein U is nitrogen substituted with a hydrogen, n is one, R is hydrogen, W is carbonyl, X and Z are hydrogen, Y is fluoro and the compound is the positively rotating enantiomer.

53. A composition according to claim 51 wherein U is nitrogen substituted with a hydrogen, n is one, R is hydrogen, W is carbonyl, X is methyl, Y is fluoro and Z is hydrogen.

54. A composition according to claim 53 wherein the compound is the positively rotating enantiomer.

55. A method for treating a diabetic host to prevent or alleviate ocular or neuritic diabetes-associated chronic complications, which comprises orally, parenterally or topically administering to said diabetic host an alleviating or prophylactically effective amount of a compound as claimed in claim 1.

56. A method according to claim 55 wherein U is nitrogen substituted with a hydrogen, n is one, R is hydrogen, W is carbonyl, X and Z are hydrogen, Y is fluoro and the compound is the positively rotating enantiomer.

57. A method according to claim 55 wherein U is nitrogen substituted with a hydrogen, n is one, R is hydrogen, W is carbonyl, X is methyl, Y is fluoro and Z is hydrogen.

58. A method according to claim 57 wherein the compound is the positively rotating enantiomer.

59. A compound according to claim 38 wherein X is methyl, Y is fluoro and Z is hydrogen.

60. A compound according to claim 59 which is the positively rotating enantiomer.

* * * * *